US005654497A

United States Patent [19]
Hoffheins et al.

[11] Patent Number: 5,654,497
[45] Date of Patent: Aug. 5, 1997

[54] MOTOR VEHICLE FUEL ANALYZER

[75] Inventors: Barbara S. Hoffheins, Knoxville; Robert J. Lauf, Oak Ridge, both of Tenn.

[73] Assignee: Lockheed Martin Energy Systems, Inc.

[21] Appl. No.: 655,664

[22] Filed: Jun. 3, 1996

Related U.S. Application Data

[63] Continuation of Ser. No. 301,147, Sep. 6, 1994, abandoned, which is a continuation-in-part of Ser. No. 845,127, Mar. 3, 1992, abandoned.

[51] Int. Cl.$^6$ .................... G01N 27/16; G08B 17/10
[52] U.S. Cl. .................... 73/23.2; 73/31.05; 364/498
[58] Field of Search .................... 73/23.31, 23.2, 73/23.41, 31.05; 395/21, 22, 24, 27; 364/498

[56] References Cited

U.S. PATENT DOCUMENTS

| | | | |
|---|---|---|---|
| 4,457,161 | 7/1984 | Iwanaga et al. | 73/31.05 |
| 4,542,640 | 9/1985 | Clifford | 73/23 |
| 4,631,952 | 12/1986 | Donaghey | 73/25.03 |
| 4,638,443 | 1/1987 | Kaneyasu et al. | 73/31.05 |
| 4,670,405 | 6/1987 | Stetter et al. | 73/23.2 |
| 4,818,348 | 4/1989 | Stetter | 73/23.2 X |
| 4,907,441 | 3/1990 | Shurmer | 73/31.05 |
| 5,106,563 | 4/1992 | Zaromb | 73/23.41 |
| 5,209,275 | 5/1993 | Akibu et al. | 73/23.2 X |

OTHER PUBLICATIONS

S. Zaromb and J. R. Stetter, *Sensors and Actuators*, 6 (1984) 225–243.

Gardner, J. W., et al "Application of Artificial Neural Networks in an Electronic Nose," *Meas. Sci. Technol.*, 1 (1990) 446–451.

Lauf et al., *Fuel*, 1991, vol. 70, Aug., pp. 935–940.

Gardner, J. S., et al (eds.) *Techniques and Mechanisms in Gas Sensing*, Chapter 14, "Pattern Recognition in Gas Sensing," Adam Hilger, Bristol, 1991, pp. 347–380.

A. Ikegami & M.Kaneyasu, "Olfactory Detection Using Integrated Sensor," Proc. of Transducers '85, 1985 Intl. Con. on Solid State Sensors & Actuators, Philadelphia, PA, 136–139, 1985.

B. S. Hoffheins, *Masters Thesis*, University of Tennessee, 1989.

J. W. Gardner, "Detection of Vapours and Odours from a Multisensor Array Using Pattern Recognition Part I. Principal Component and Cluster Analysis," Sensors and Actuators B, vol. 4, 109–115, 1991.

P. N. Bartlett, "The Design of an Artificial Olfactory System," Paper No. 253, Pittsburgh Conference, Chicago, Mar. 1991.

"Determination of Fuel Properties," *Research Disclosure*, pp. 571–572, 1991.

*80170W Electronically Trainable Analog Neural network*, Experimental Report, Intel Corp., Santa Clara, CA, May 1990.

MD1220 Neural Bit Slice, Data Sheet, Micro Devices Corp., Lake Mary, FL, Mar. 1990.

ANSim User's Manual, Chapters 1, 3 (no date).

*Primary Examiner*—Michael Brock
*Attorney, Agent, or Firm*—W. Mark Bielawski; James M. Spicer; Harold W. Adams

[57] ABSTRACT

A gas detecting system for classifying the type of liquid fuel in a container or tank. The system includes a plurality of semiconductor gas sensors, each of which differs from the other in its response to various organic vapors. The system includes a means of processing the responses of the plurality of sensors such that the responses to any particular organic substance or mixture is sufficiently distinctive to constitute a recognizable "signature". The signature of known substances are collected and divided into two classes based on some other known characteristic of the substances. A pattern recognition system classifies the signature of an unknown substance with reference to the two user-defined classes, thereby classifying the unknown substance with regard to the characteristic of interest, such as its suitability for a particular use.

29 Claims, 14 Drawing Sheets

MOTOR VEHICLE FUEL ANALYZER

This application is a continuation of application Ser. No. 08/301,147, filed Sep. 6, 1994, now abandoned, which is a continuation in part of application Ser. No. 07/845,127, filed Mar. 3, 1992, now abandoned.

This invention was made with Government support under contract no. DE-AC05-84OR21400 awarded by the U.S. Department of Energy. The research was funded through the Office of Arms Control (DP-5), Systems and Technology Division. The Government has certain rights in this invention.

BACKGROUND OF THE INVENTION

1. Field of the Invention

The invention relates generally to systems for identifying organic liquids, and more particularly to a field-utilizable analytical instrument using a semiconductor gas sensor array and neural network processor to identify and characterize liquid fuels.

There is an increasing demand for small, rugged and portable instruments to identify organic substances in the field. In particular, there is need for a field instrument capable of rapid, on-site analysis and identification of aviation and automotive fuels. Some of the applications for such an instrument are ensuring that an aircraft is refueled with the correct grade of fuel, checking gasoline at the point of sale for alcohol and/or octane number (ON), and verifying that fuel storage facilities contain the proper grades of fuel. All of these needs as well as other safety-related applications would be met by an instrument capable of quick determinations of fuel type and octane number in the field.

The usual test for octane number is the rigorous CFR test which is based on running the fuel through an internal combustion engine, and requires sophisticated equipment and hours of setup time. Laboratory-grade instruments normally used in conjunction with octane number measurements may involve infrared spectrum analysis, multivariate regression analysis, flame reactions, mass spectrometers, gas chromatographs, microprocessor-controlled octane analyzers, and others. The laboratory instruments often have the capability to analyze a large number of compounds at low concentrations, but generally are too cumbersome for field use and often require time-consuming sample preparation as well.

2. Description of the Prior Art

The first examples of prior art involve gas sensor arrays coupled with pattern recognition approaches to identify unknown gas samples. The first of these (P. K. Clifford, "Selective Gas Detection and Measurement System", U.S. Pat. No. 4,542,640, Issued Sep. 24, 1985), is a chemometric approach that relies on the solution of linear equations. Clifford's method is unsuitable when dealing with liquid fuels, which may have tens or hundreds of individual organic constituents. Clifford's approach also requires that the number of sensors be greater than or equal to the number of unknown gases. The second example (A. Ikegami and M. Kaneyasu, "Olfactory Detection Using Integrated Sensor", *Proc. of Transducers '85*, 1985 Intl. Conf. on Solid State Sensors and Actuators, Philadelphia, Pa., 136–139, 1985), uses a microcomputer to mathematically calculate the similarities in patterns of certain essentially pure substances that are not necessarily chemically similar.

Recent work by B. S. Hoffheins at the Oak Ridge National Laboratory showed that the problem of qualitative gas analysis of a few essentially pure substances can be greatly simplified through the use of semiconductor gas sensors together with pattern recognition and/or neural networks (B. S. Hoffheins, Master's Thesis, University of Tennessee, 1989). Hoffheins reported results of using a nine sensor array with a neural network to analyze the patterns of a six item group comprising isopropanol, methanol, ethanol, heptane, hexane, and hexane-2% ethanol. In addition, an integrated sensor array was used to obtain patterns of one gasoline sample and samples of the same gasoline with either methanol or ethanol added to it. Although slight differences were noted in the patterns, no attempt was made to classify the gasoline samples with a neural network.

In 1991, Gardner and Bartlett in separate papers reported results similar to Hoffheins (J. W. Gardner, "Detection of Vapours and Odours from a Multisensor Array Using Pattern Recognition Part I. Principal Component and Cluster Analysis", *Sensors and Actuators B*, Vol 4, 109–115, 1991), (P. N. Bartlett, "The Design of an Artificial Olfactory System," Paper no. 253, *Pittsburgh Conference*, Chicago, March 1991).

Also in 1991, anonymous authors reported applying a neural network to the spectroscopic analysis of infrared data ("Determination of Fuel Properties", *Research Disclosure*, pp. 571–572, 1991). This last reference appears to be the first attempt to produce an instrument designed specifically for determination of octane number by indirect means, that is, without actually burning the fuel in an engine and observing knock characteristics.

OBJECTS

It is a principal object of this invention to provide a system for rapid and convenient analysis of complex gas mixtures that are chemically similar.

Another principal object of this invention is to provide a selective analysis system for fuels, particularly those used in aviation and automobiles.

A third principal object of this invention is to provide a selective analysis system for classifying the signatures of a plurality of fuels using a fewer number of sensors than fuels.

It is also an object of this invention to provide a rapid analysis system for classifying fuels according to octane number or suitability for a particular vehicle, engine, or class of vehicles.

Another object of the invention is to provide a fuel inspection method that is more convenient than the CFR engine method.

Yet another object of this invention is to provide a fuel analysis system that eliminates tedious calibration processes and extensive numerical calculations.

A further object of the invention is to provide an analysis system for complex organic substances that is not limited to simple, essentially pure compounds.

SUMMARY OF THE INVENTION

The rapid fuel analysis instrument works on the principle that an array of gas sensors will react to fuel vapors in such a way that each fuel has a distinctive signature. The signatures are then "learned" by a neural network. When an unknown sample is tested, the neural network examines the signature and determines the closest match to the known patterns. The sensor head contains ten commercial metal oxide gas sensors. The measured parameter is the resistance of the metal oxide, which decreases in the presence of organic or reducing vapors. Nine of the sensors are nominally identical, except their heaters are powered at different levels. This causes the sensors to react differently to the vapor sample present in the sensor chamber. The tenth sensor has a different combination of metal oxide and catalyst; consequently, its characteristic response can be quite different from the other sensors. The signature for a sample comprises the resistance readings taken from all ten sensors simultaneously. Signatures from the sensor array are scaled by an analog-to-digital (A/D) converter and transformed into binary bit patterns, one for each sample gas. Each pattern consists of a coded matrix, which is an appropriate size for the problem at hand. A pattern size used was 1×16 for each sensor, or 10×16 for the ten sensors. A smaller pattern size can be used if fewer sensors are needed to determine the identity of substances in a particular application. Alternatively, the size can be larger to increase the power of resolving the different signatures. A collection of these bit patterns from each of the possible substances in a problem set, called training vectors, is used to train the neural network. A neural network simulation program called ANSim™, developed by Science Applications International Corporation, San Diego, was used. Once the neural network "learns" the training vector set, it can identify patterns from unknown samples. Collecting the signature of an unknown sample takes about five minutes; identification of the signature is virtually instantaneous. Samples require no special preparation.

DETAILED DESCRIPTION OF THE INVENTION

Figure 1:
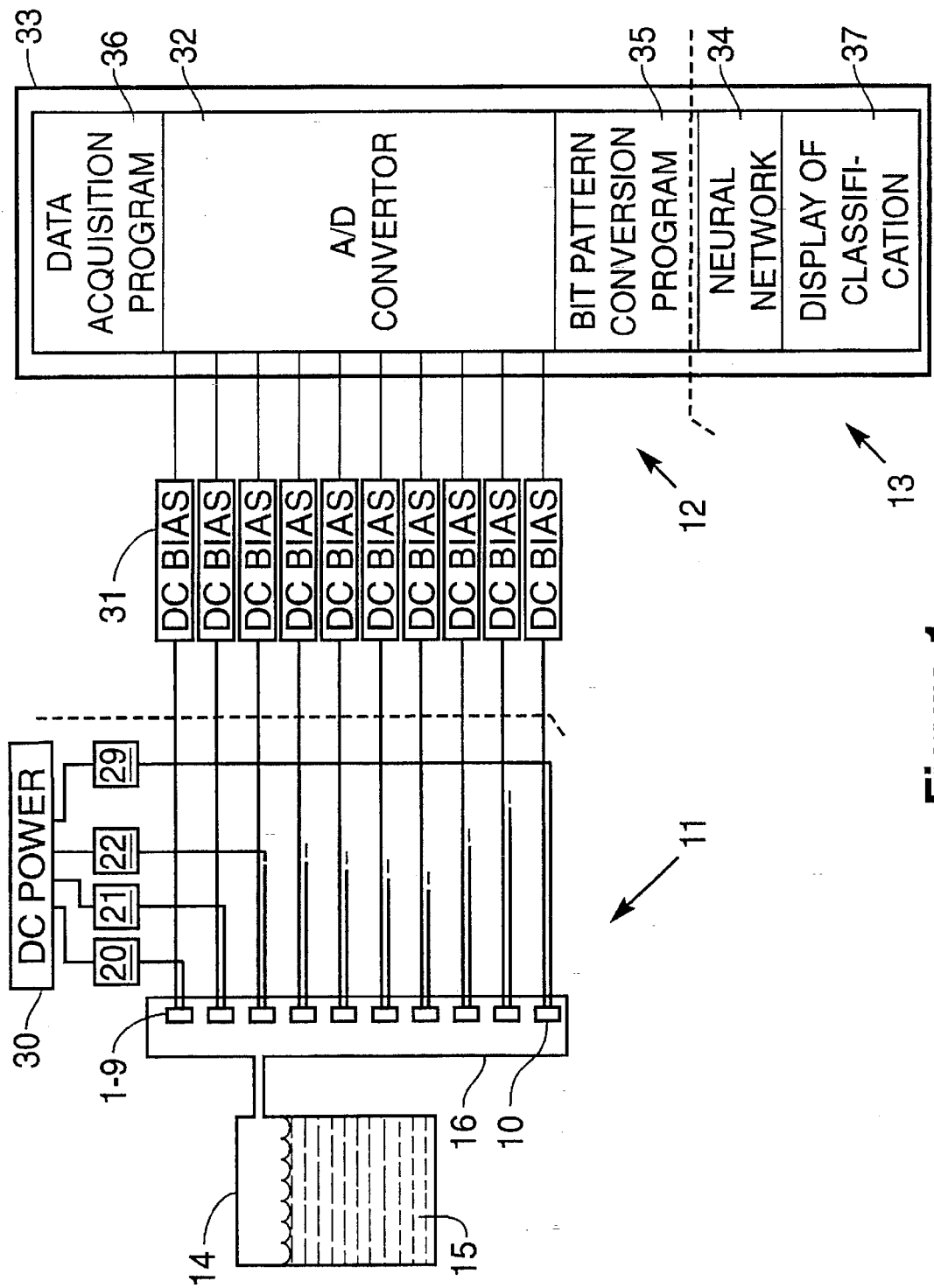
FIG. 1 is a block diagram showing an embodiment of the present invention.

FIG. 1 illustrates a gas sensor array 11, data acquisition system 12, and data analysis system 13 for the classification of volatile fuels according to the invention. In the figure, a chamber 14 contains the fuel 15 being tested. If desired, humid air may be passed through the chamber 14 in order to pick up fuel vapor and move it to chamber 16, which contains the gas sensor array 11. Sensing elements comprising commercially-available semiconductor gas sensors 1–10 are exposed to the vapors from the fuel 15. D.C. power is supplied to the heater of each sensor 1–10 through individual voltage divider networks 20–29 connected to a D.C. power supply 30. Each heater network 20–29 can be individually adjusted, a useful feature for tuning each sensor's sensitivity for a particular problem set. Sensor outputs are D.C. biased (31) to conform to the input requirements of a multiple channel analog-to-digital (A/D) data acquisition board 32 in a personal digital computer 33.

In the computer 33, a commercial neural network simulation program 34 called ANSim™ was used for classification of the fuel signatures (ANSim™, Science Applications International Corp., San Diego, Calif., 1987). In addition to the commercial neural network processor 34, two other computer programs are used in the invention. A bit pattern conversion program 35, written in the C language, is used to store and transform data from the A/D convertor 32 to bit patterns for use by the neural network 34. A second computer program 36, written in GW Basic, facilitates the data acquisition process in the computer 33. Copies of the two programs are included in the Appendix hereto.

Among the several neural network paradigms available in the ANSim™ system, three autocorrelation paradigms (Hopfield, Hamming and Boltzmann) were chosen because they retrieve patterns most like the input pattern presented to them. The operation of these networks also most closely fits the operation of the gas sensor array detector; that is, the stored patterns would be the possible choices to which the input pattern would be compared. Generally, the Hamming and Boltzmann networks represent improvements over the operation of the Hopfield network and they have better success with the identification problem. The final element of the invention is a display means 37 for presenting the results of the classification to the user. The ANSim™ program provides side-by-side graphical displays of the sample pattern being tested and the training vector or pattern it most closely resembles. The ANSim™ program also provides a listing of names of all the samples the network has been trained on, and indicates which sample is the closest match to the sample under test.

One sensor array used in tests to date comprised 10 discrete commercial Taguchi-type tin oxide sensors. A Taguchi-type metal oxide sensor exhibits a large change in resistance in the presence of gases to which it is sensitive. The resistance of the sensors used in this work were observed to decrease by four to five orders of magnitude when exposed to alcohol vapor, for example. Nine of the sensors (1–9) were the Figaro Engineering Model TGS 812, and were operated at power levels ranging from 100% (sensor 1) to 27% (sensor 9) of the manufacturer's recommended operating power (900 mW). Sensor 10, a Figaro Model TGS 824, was operated at 100% power. Table I gives the sensor power levels in detail.

TABLE 1

Operating characteristics of the ten sensor array

| Sensor | Model | % Rated Power |
|---|---|---|
| 1 | TGS 812 | 100 |
| 2 | TGS 812 | 90 |
| 3 | TGS 812 | 80 |
| 4 | TGS 812 | 70 |
| 5 | TGS 812 | 60 |
| 6 | TGS 812 | 50 |
| 7 | TGS 812 | 40 |
| 8 | TGS 812 | 30 |
| 9 | TGS 812 | 27 |
| 10 | TGS 824 | 100 |

This is only one of many sensor arrangements. In addition to using nominally identical sensors operated at different power levels (and therefore different temperatures), different models of sensors can be used in the array. Many examples of sensor arrays composed of discrete sensors and miniature integrated sensor arrays on a single substrate have been described in the literature. Clifford, for example, described the value of homogeneous semiconductor gas sensors, sensors that vary according to their composition, and sensors that vary according to their operating temperature, etc. The general rule is to ensure that each element (sensor) of the array will have different response characteristics for the problem set of gases being examined. With such a variety of sensors and operating modes, the user can have wide control over the range of sensitivities of the different sensing elements, thereby allowing the method to be optimized for a given analysis problem.

Figure 2:
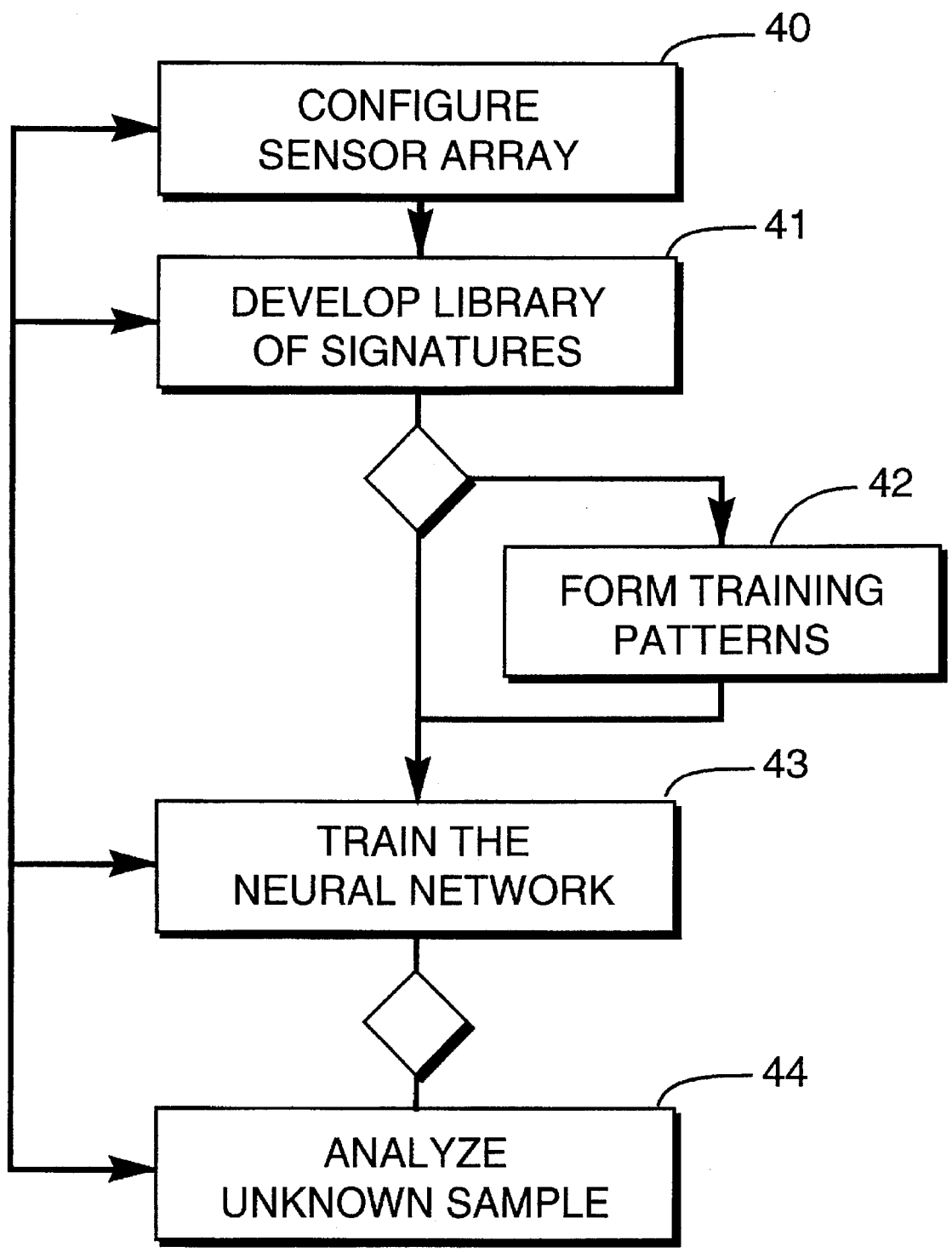
FIG. 2 is a flowchart of the method of this invention.

The method of operation of the invention will be more clearly described with reference to FIG. 2. FIG. 2 shows the process by which parameters for configuring an instrument for a specific application are obtained. The process consists of a series of steps, which are taken in order, and which may require multiple passes through all or part of the steps in order to refine and optimize the system for a particular instrument application.

The process begins with the selection of a sensor array (step 40). Sensors that are known to be sensitive to the problem substances should be chosen, as well as sensors that respond less strongly. Also, at this step, several sensors of one model might be included in the array, but each one operated at different temperatures as previously described, in order to study the range of possible responses. At this initial step 40, one should not be concerned with limiting the size of the sensor array. Following sensor selection, the sensor array is tested with the possible or typical species expected in the problem system and a library of signatures is developed (step 41, see also FIGS. 3 and 4). At this step, sensors that do not respond at all might be dropped from the array. Also, sensors giving redundant information could be eliminated. The next step, forming training patterns (step 42), is optional if the neural network can accept as training patterns the kind of data represented by the signatures; otherwise, some conversion routine is performed to transform the data into input to the neural network 34. In the case of the ANSim™ neural network software, such a step 42 was required, and Applicants' bit pattern conversion program 35 was written to transform the signatures to two-dimensional bit patterns for input to the neural network 34. Whether in the form of signatures, bit patterns, or some other suitable arrangement, training patterns consist of a set of patterns, each of which represents a particular outcome or combination of outcomes for presentation to the neural network 34.

Some neural network training systems require only one training pattern per class, others may accept several patterns offered as members of one class. In any event, the training step 43 is part of the operation of whichever neural network 34 is used. In this step, the training patterns are presented to the neural network which "learns" the patterns and thereby defines the limit of each class. The ability of the neural network 34 to classify the set of training patterns is evaluated at this step by checking its ability to classify its own training set and then by testing its ability to identify "unknown" samples as well. If the neural network does not perform adequately, one may elect to a) improve the uniqueness of the sensor array responses by changing the sensors or their operation (return to step 40), b) redesign the library of signatures and training patterns for improved performance (steps 41 and/or 42), or c) examine the neural network for improved performance. If the neural network classifies the full signatures, and instrument simplicity is also important, the sensor array should be examined to determine which sensors can be eliminated without degrading neural network performance.

It is expected that several passes through steps 40–43 will be required, during which the sensor parameters are modified until an optimized system is attained. It is realized that in general, the better the neural network is at classification, the more drift and variation it can tolerate from the sensor array patterns. In contrast, if the information from the sensor array is very reliable, and each signature is very distinctive, then the neural network does not have to be as powerful. With the neural network "trained", the only step remaining is that of analyzing an unknown sample (step 44), a step that is inherent in any neural network program, but which comprises analyzing the unknown sample against the library of signatures or training patterns as may be the case, and classifying it with respect to the storm signatures or training patterns.

In all of the instrument applications cited above, one has access to a large concentration of the fuel vapors of interest, for instance, in the headspace of a storage tank. The use of high concentrations of vapor makes the process somewhat faster and more reproducible. It is, in principle, possible to use the inventive technique with lower vapor concentrations provided that the neural network has been trained with signatures of each fuel at each expected concentration, and the signature of one fuel at one concentration does not resemble that of a different fuel at another concentration. There is, in any case, a lower concentration limit below which classification will become unreliable.

RESULTS AND DISCUSSION

Aviation fuels

The aviation fuels examined here (Table 2) include several civilian and military grades of jet fuel as well as a high-octane low lead gasoline.

TABLE 2

| Aviation Fuels | |
|---|---|
| Fuel Type | Source/Manufacturer |
| Jet A | Cherokee Aviation/Exxon |
| Jet A + deicer (Philjet A55MB) | Cherokee Aviation/Phillips |
| JP-4 | Tennessee Air National Guard |
| JP-5 | Exxon |
| JP-7 standard | Exxon |
| JP-7 thermally stable | Exxon |
| Gasoline grade 100LL | Cherokee Aviation/Phillips |

Although most jet fuels are based on the kerosene fraction (150°–288° C. boiling range), the actual composition of a fuel is determined to a large degree by the nature of the crude oil from which it is derived. For aviation grades, the kerosene fraction contains at least 75% saturates and no more than 25% aromatics. Depending on the crude, the saturated fraction (75%) contains from 10 to 60% straight-chain paraffins with the balance composed of various cycloparaffins. In the aromatic fraction (25%), the ratio of single- to multi-ring compounds also varies considerably.

About 95% of civil aviation uses a kerosene-type fuel (Jet A and Jet A-1). Jet A-1 is similar to Jet A but has a slightly lower freezing point for long-duration international flights. A wide-cut fuel (Jet-B) is available for severe arctic use.

A wide-cut fuel (JP-4) was developed by the U.S. Air Force in order to assure the availability of large volumes of fuel during national emergencies. The U.S. Navy uses kerosene with a higher flash point (JP-5) because of the special safety requirements for use on aircraft carriers. JP-7 is a high flash point special kerosene used in advanced supersonic aircraft and is available in both regular and thermally stable versions. JP-8 is a developmental kerosene fuel similar to Jet A-1.

Aviation gasolines also vary somewhat depending on the source of the crude oil and refining method. Relevant properties are specified in ASTM specification D 910-82.

Motor fuels

Gasoline, like jet fuel, is a highly variable mixture whose chemical composition and properties can vary widely depending on crude source, refining process, seasonal factors, etc. Among the many fuel samples that were collected, four grades were examined in detail to determine if the method could detect the two most basic differences, namely octane number (ON) and the presence of alcohol. Three grades of unleaded gasoline were used representing the octane numbers 87, 89, and 92, as well as one grade of gasoline containing 10% ethanol.

EXAMPLE 1

10 Taguchi-Type Sensors, 7 Aviation Fuels

Figure 3:
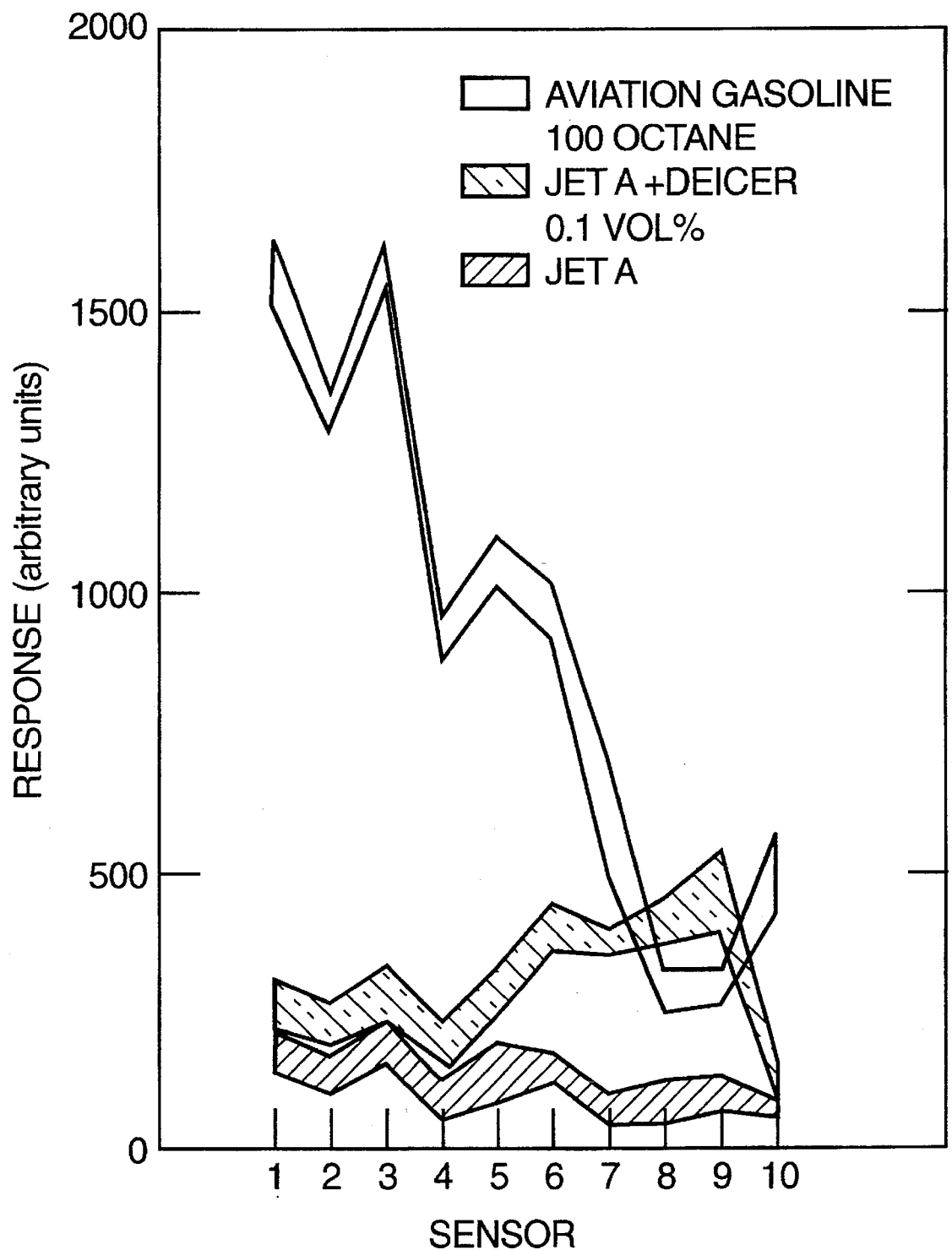
FIG. 3 is a graph illustrating the signatures of three civil aviation fuels.
Figure 4:
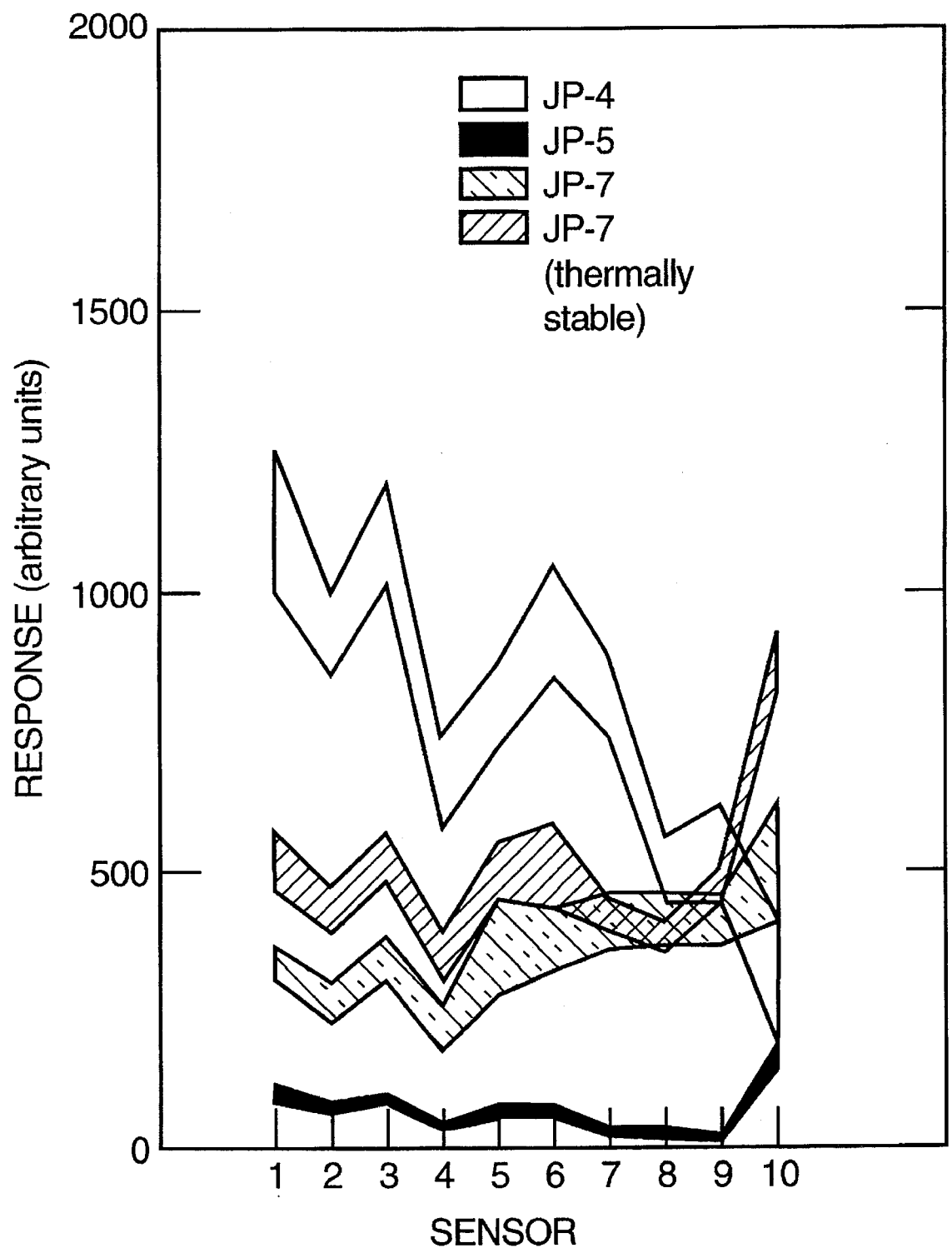
FIG. 4 is a graph illustrating the signatures of four military aviation fuels.
Figure 5:
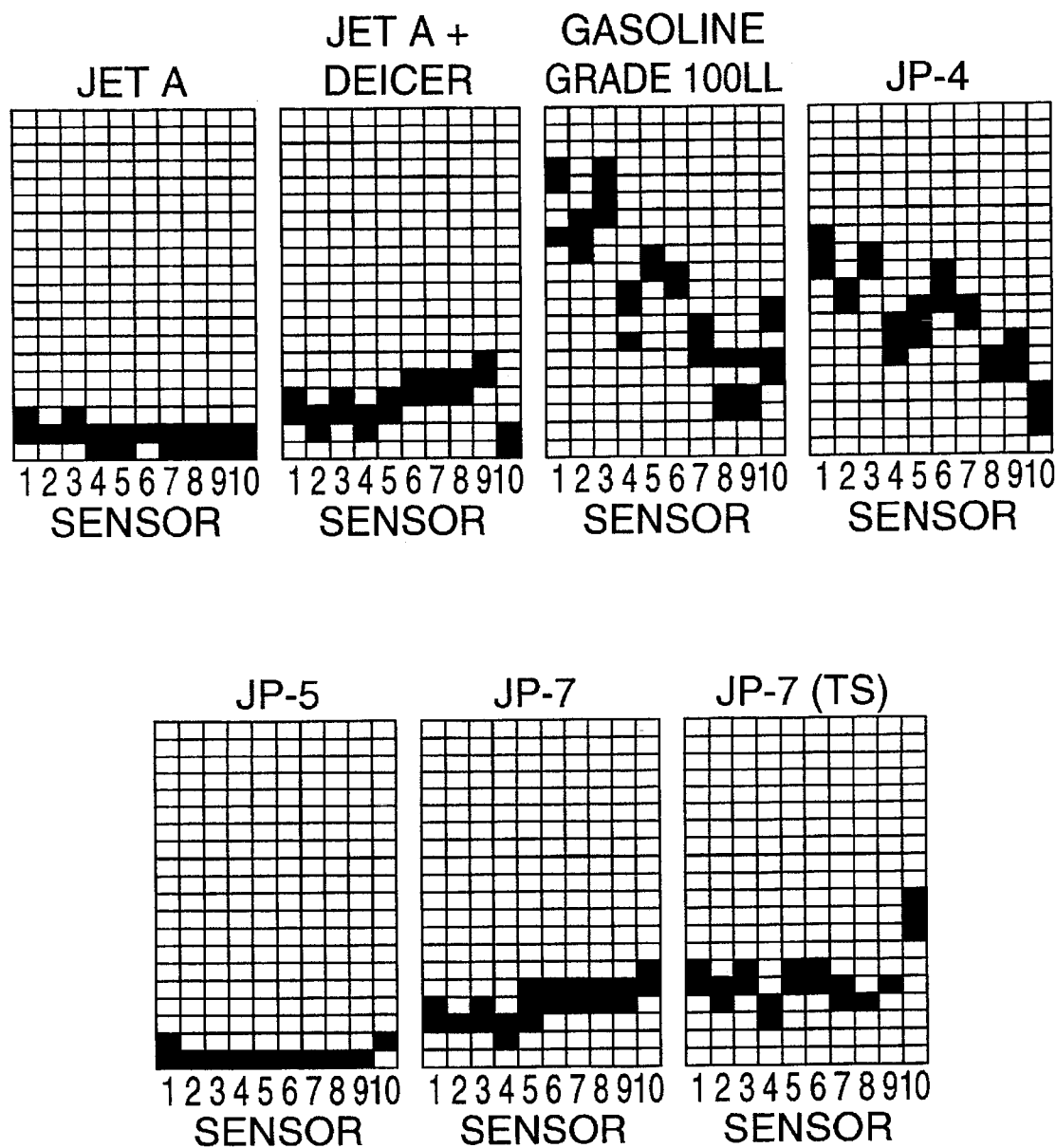
FIG. 5 is a graph illustrating the bit patterns of the seven aviation fuels of FIGS. 3 and 4.

The uniqueness and reproducibility of the signatures of several aviation fuels can be seen by inspection of FIGS. 3 and 4. In these figures are plotted on a common scale the responses (signatures) of the ten-sensor array described above to three commercial aviation fuels and four military fuels, respectively. Each signature represents the maximum range of 5- and 10-minute readings observed in several runs (typically three runs of each fuel). The ran-to-run variations in any one signature, indicated by the shading, are small relative to the differences between one signature and another. Perhaps the most striking result is the difference between the signatures of Jet A with and without 0.1% deicer. These two fuels look and smell alike, and therefore could not be readily distinguished by an operator without some kind of analysis. The signature of aviation gasoline is substantially different from the kerosene-type fuels as one would expect. The signature of JP-4 showed some similarity to that of gasoline, as expected, since it contains significant amounts of naphtha-range light hydrocarbons. FIG. 5 shows the effect of step 42, i.e., that of transforming the signatures into bit patterns by the bit pattern conversion program 35. These bit patterns are sufficiently different and could be learned and recognized by the neural network.

EXAMPLE 2

10 Taguchi-Type Sensors, 4 Motor Fuels

Figure 6:
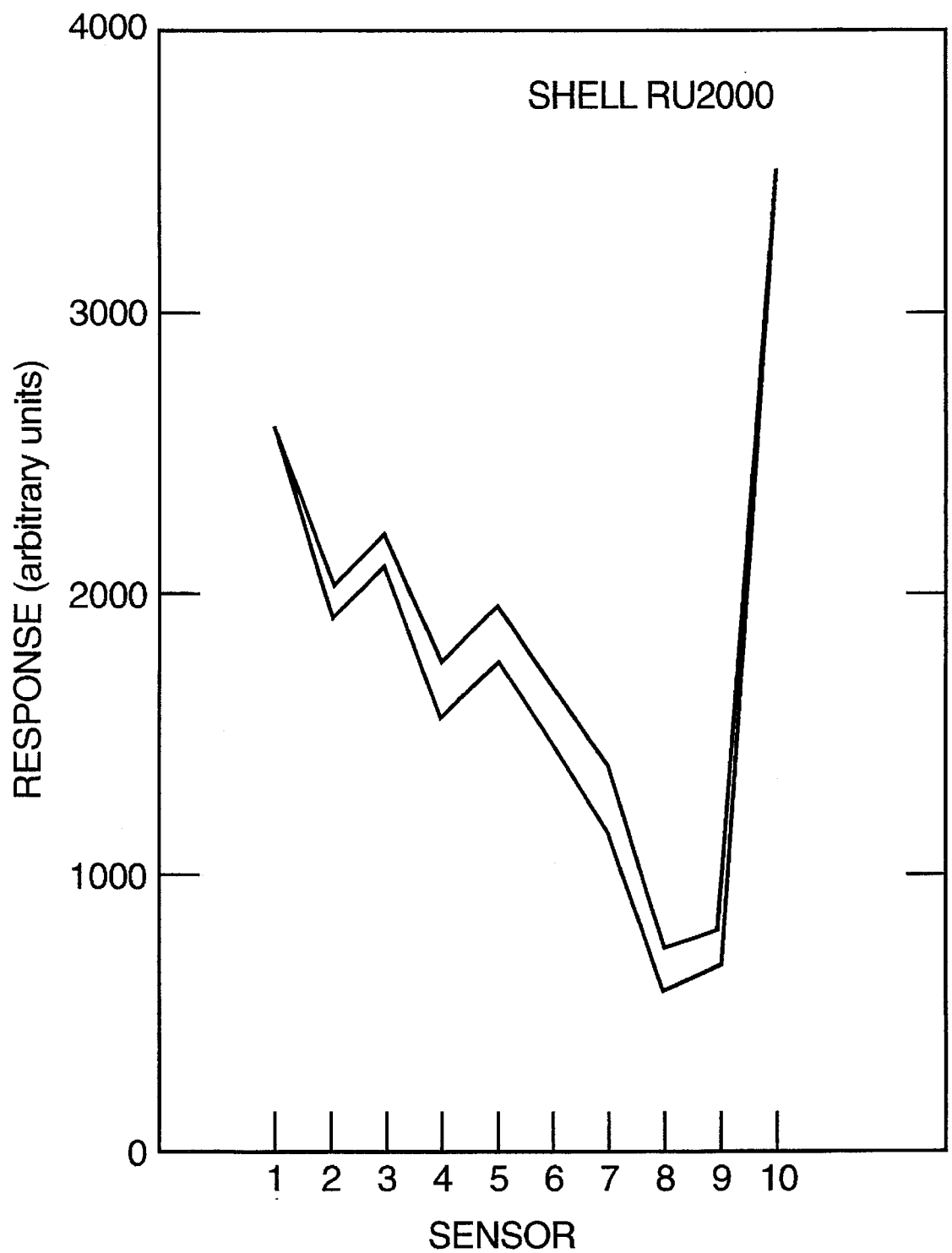
FIG. 6 is a graph illustrating the signature of an 87 ON motor fuel.

The same ten-sensor array described in the previous example was tested with three grades of unleaded gasoline, 87 ON, 89 ON, 92 ON, and gasoline/ethanol blends from different gasoline suppliers. The signatures, FIGS. 6–9, were converted to 10×16-bit patterns as before. Patterns derived from signatures of Shell RU-2000 (87 ON), SR-2000 (89 ON), SU-2000 (92 ON), and gasoline containing 10% ethanol (Citgo 93 ON), respectively, were used to train the neural network. The neural network easily distinguished between straight gasoline and alcohol-containing blends. Surprisingly, the network correctly classified fuel samples having the highest and lowest ON, even through the raw signatures of these fuels look very similar to the eye (FIG. 6 and FIG. 8).

EXAMPLE 3

7 Taguchi-Type Sensors, 4 Motor Fuels

A seven-sensor array was constructed from the ten-sensor array in the previous example by eliminating sensors 8, 9, and 10. The pattern size was 7×16 bits. Surprisingly, results of the seven sensor configuration were not greatly different from that of the 10-sensor array described earlier. These results are unexpectedly good given the size of the pattern and the visual similarity of all the straight gasoline fuel signatures. With larger sample sizes, the performance of this instrument would be further improved.

EXAMPLE 4

3 Taguchi-Type Sensors, 7 Aviation Fuels

Figure 10:
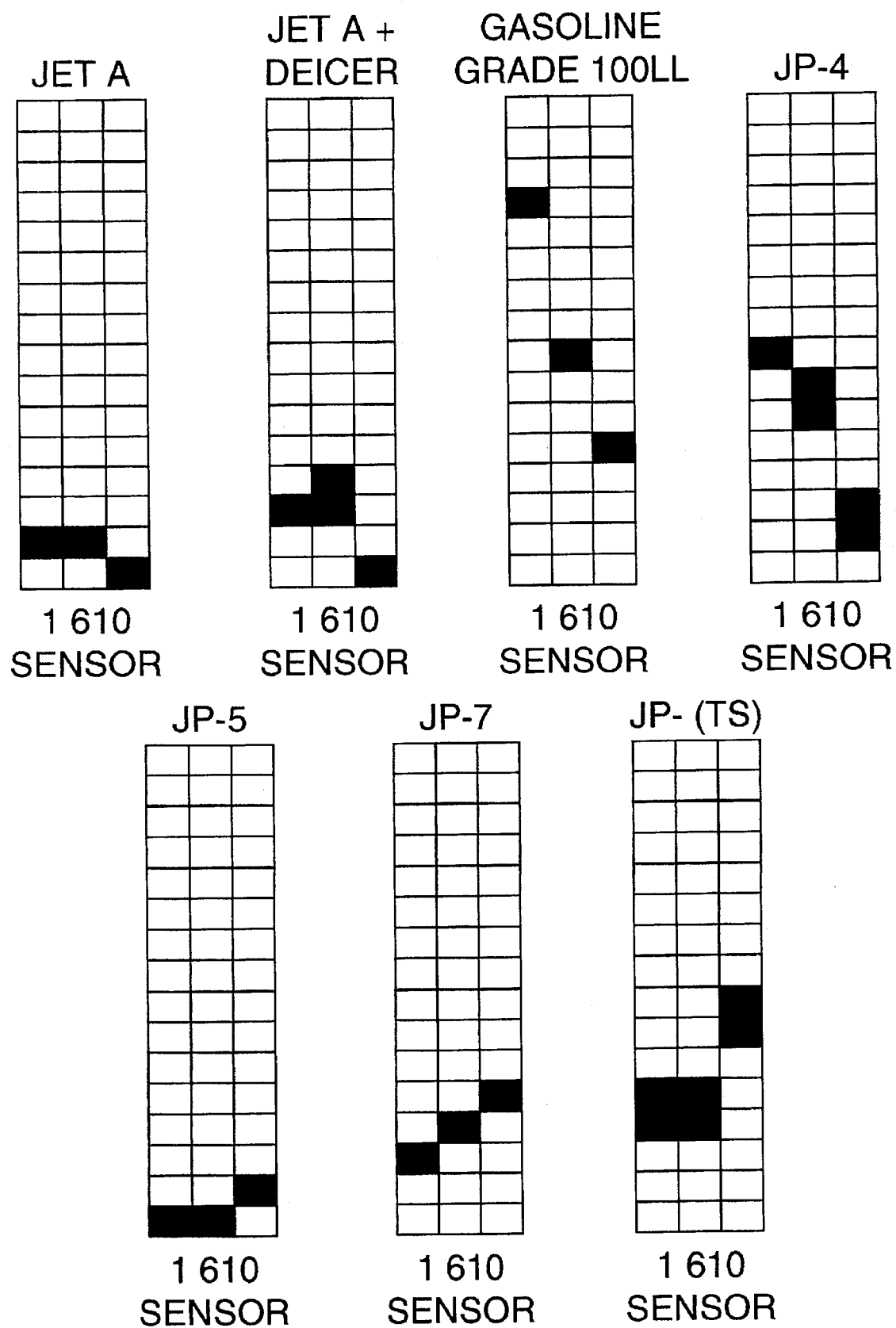
FIG. 10 is a graph illustrating the bit patterns of the seven aviation fuels of FIGS. 3 and 4 using only three sensors.

A three-sensor array was constructed by eliminating four additional sensors from Example 3 so that only sensors 1, 6, and 10 remained. The 3×16 bit patterns for the same aviation fuels as Example 1 are shown in FIG. 10. The data for sensors 1, 6, and 10 in FIGS. 5 and 10 are the same. Surprisingly, the neural network trained with the three-sensor data set (the 3×16 bit patterns) from the aviation fuel signatures performed fairly well. Examples 3 and 4 demonstrate that Clifford's requirement in U.S. Pat. No. 4,542,640 that the number of sensors exceed the number of unknowns does not apply in Applicants' neural network method when the substances of interest have distinct and reproducible signatures.

EXAMPLE 5

3 Taguchi-Type Sensors, 4 Motor Fuels

Because the differences in the signatures of motor fuels are more subtle, this particular three-sensor array was not able to classify automobile gasolines as to their octane level. It did, however, successfully differentiate between gasoline and gasohol.

In focusing on the development of sensor arrays and pattern recognition system for portable instruments, Applicants recognize that minimization of power consumption and simplification of the pattern recognition system are two important concerns. Most of the power consumption is by the metal-oxide type sensors, which typically consume 300–900 mW when operated at full power. Power consumption can be reduced by minimizing the number of discrete sensors in the array or by miniaturizing the array.

Incorporating the pattern recognition approach into hardware might be done several ways. A sensor testbed, such as described herein, can help identify a viable approach and define system parameters. Special-purpose devices such as neural network chips are becoming available and, if successfully implemented, would replace several general-purpose chips, thereby simplifying the overall design. An Intel chip ("80170NW Electronically Trainable Analog Neural Network," Experimental Report, Intel Corp., Santa Clara, Calif., May 1990) is a more general purpose device that can be programmed many ways. A Micro Devices chip ("MD1220 Neural Bit Slice," Data Sheet, Micro Devices Corp., Lake Mary, Fla., March 1990) could be used for a problem set of eight patterns, or up to eight chips could be connected to address a problem set of 256 patterns. Chemometric algorithms such as Clifford's, sized properly, could be coded into microprocessor devices. Also, both neural network and chemometric algorithms, sized for the problem set, could be incorporated into application-specific integrated circuits. Besides a portable battery-powered implementation of this invention using miniaturized components, the technology could also be incorporated into aircraft and other large vehicles (such as tanks) to provide a check against inadvertent misfueling. A possible large-scale use is in regulatory procedures such as spot-checking gasoline at the point of sale for improper labeling as to octane rating and alcohol content.

As an analytical instrument, a neural network and optimized sensor array using this methodology can classify an unknown sample in five to ten minutes. Compared with the rigorous "Comparative Fuel Research Engine Test for Octane Number", and "Standard Test Method for Knock Characteristics of Motor Fuels by the Motor Method," which require sophisticated equipment, running the fuel in an internal combustion engine, and hours of setup time, the neural network method of this invention is a time-saving and relatively inexpensive arrangement for regulatory screening tests in the field. Suspect samples could be taken back to a laboratory for testing by the CFR engine technique, if desired.

As will be apparent from the discussion herein, minimizing the number of sensors will minimize power consumption and data processing requirements. In some instances, a few sensors can produce a set of signatures which can be recognized by very simple circuitry without even applying the invention at all. For example, two sensors may be enough to unambiguously distinguish gasoline from gasohol as was predicted in B. S. Hoffheins' Master's Thesis. In such a case, there would be no pattern recognition as such, and no use of a neural network.

The sensor array approach can be successfully applied to complex mixtures such as fuels. Although the sensor arrays in this work were not optimized, relatively simple neural network techniques can classify aviation and motor fuels. With signatures that exhibit a high degree of variability, such as the aviation fuels, successful classification could be obtained by using very few carefully chosen sensors. With signatures that are much closer in range and behavior, such as those of the motor fuels, a greater number of sensors is needed for reliable classification. Surprisingly, a 7-sensor array performed as well as the 10-sensor array for the classification of a set of motor fuels, indicating that three of the sensors were providing redundant information.

One safety-related application of the detecting system of this invention may include a plurality of sensor arrays, each in its own sensor head and dispersed in separate locations about an environment. A central computer would be responsive to signals derived from all the sensors of all the heads to determine the identities of mixtures present at each of the sensor head locations. It will be understood that fuels such as gasoline, diesel fuel, aviation fuel, or gasohol are considered to be within the scope of this invention. Also, the liquid fuels classification may be based on octane number, octane number, or alcohol content.

Using the method of FIG. 2, optimization of the sensor array and pattern recognition methods can be performed iteratively to develop and verify an application-specific system. As the set of patterns becomes more distinctive, it is likely that less resolution is needed by the pattern recognition portion; alternatively, the better the pattern recognition section, the more ambiguous the sensor output can be. With appropriate testing and characterization of the sensor arrays, and a suitable database of signatures, one can fully optimize a miniature field instrument for any given analysis and identification problem.

Figure 11:
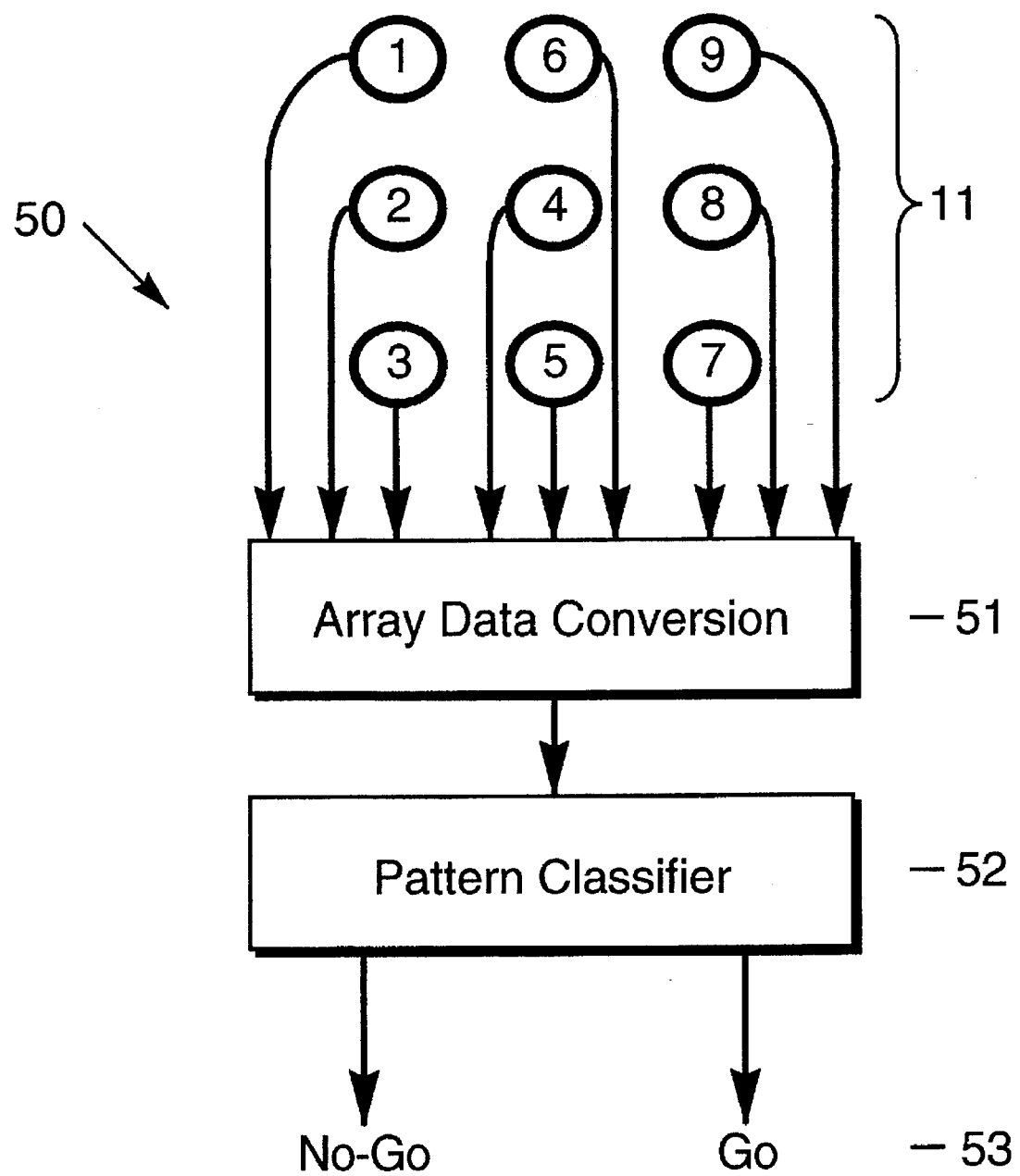
FIG. 11 is a block diagram of a simplified embodiment of the present invention to be used for screening purposes.

There are many instances in which the analysis of an unknown fuel must address only one question, viz., whether or not that fuel can be used safely in a particular vehicle. For example, highly mobile military forces wishing to exploit a captured fuel supply must determine if the fuel is suitable for a helicopter, armored vehicle, etc. For these applications, the device and method can be further simplified as shown in FIG. 11. The device 50 comprises a sensor array 11, a data acquisition and conversion system 51 which may or may not contain an analog-to-digital convertor, a pattern classifier 52, and an output system 53 capable of providing a go/no-go type of display (e.g., red and green LEDs or the like). In this case, therefore, the pattern classifier places the sensor array output into one of only two classes, viz., fuels of the desired type and fuels not of the desired type. It will be obvious to those skilled in the art that the pattern classifier can be made more or less selective depending on the demands of a particular application. The go/no-go output eliminates the need for operator judgment or interpretation.

Figure 12:
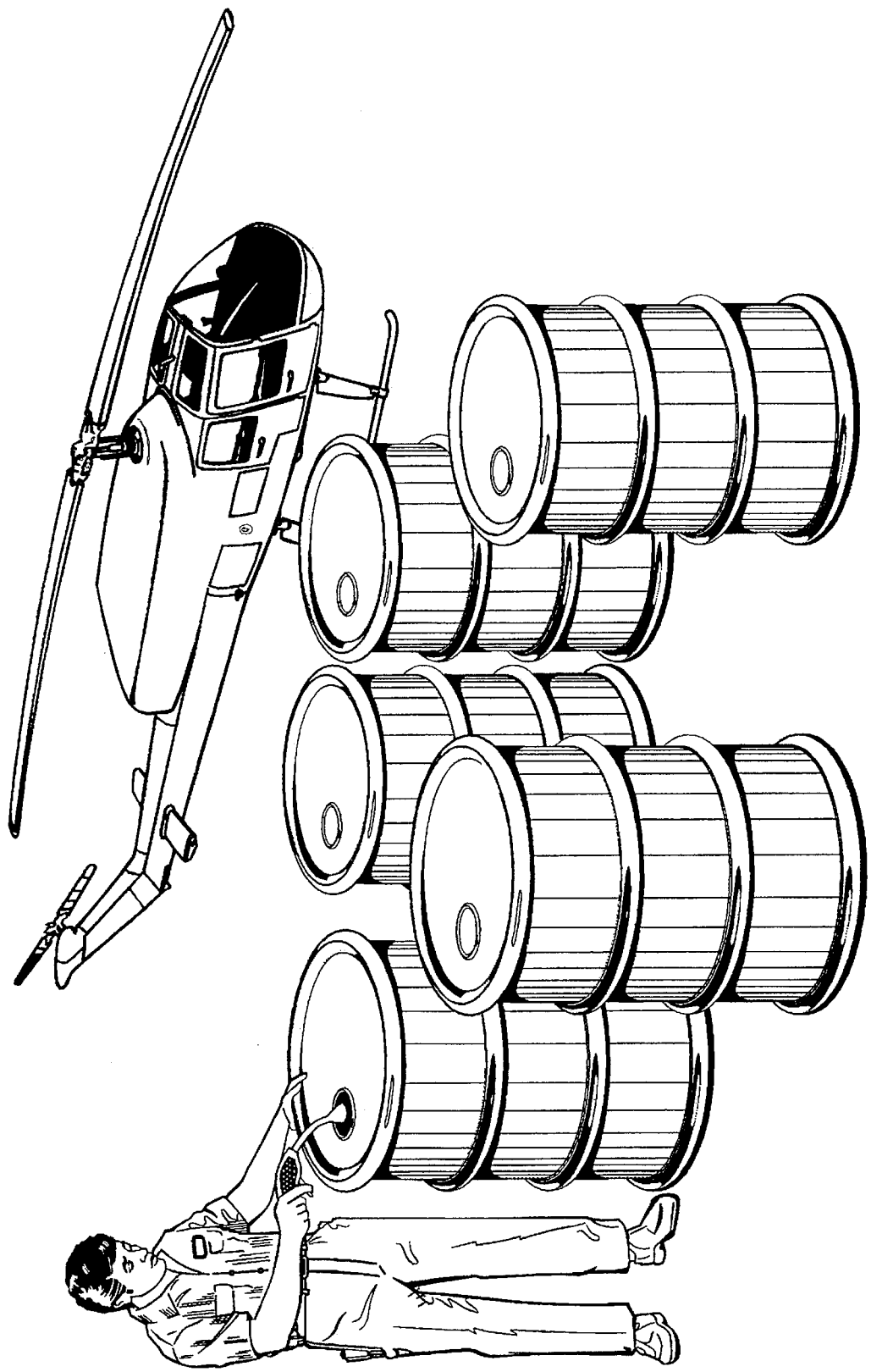
FIG. 12 illustrates the use of the present invention to inspect an unknown fuel supply.

FIG. 12 shows an embodiment of the present invention in which a technician inspects a tank of captured fuel in support of a helicopter awaiting refueling. In this embodiment, the device is completely portable and self-contained.

Figure 13:
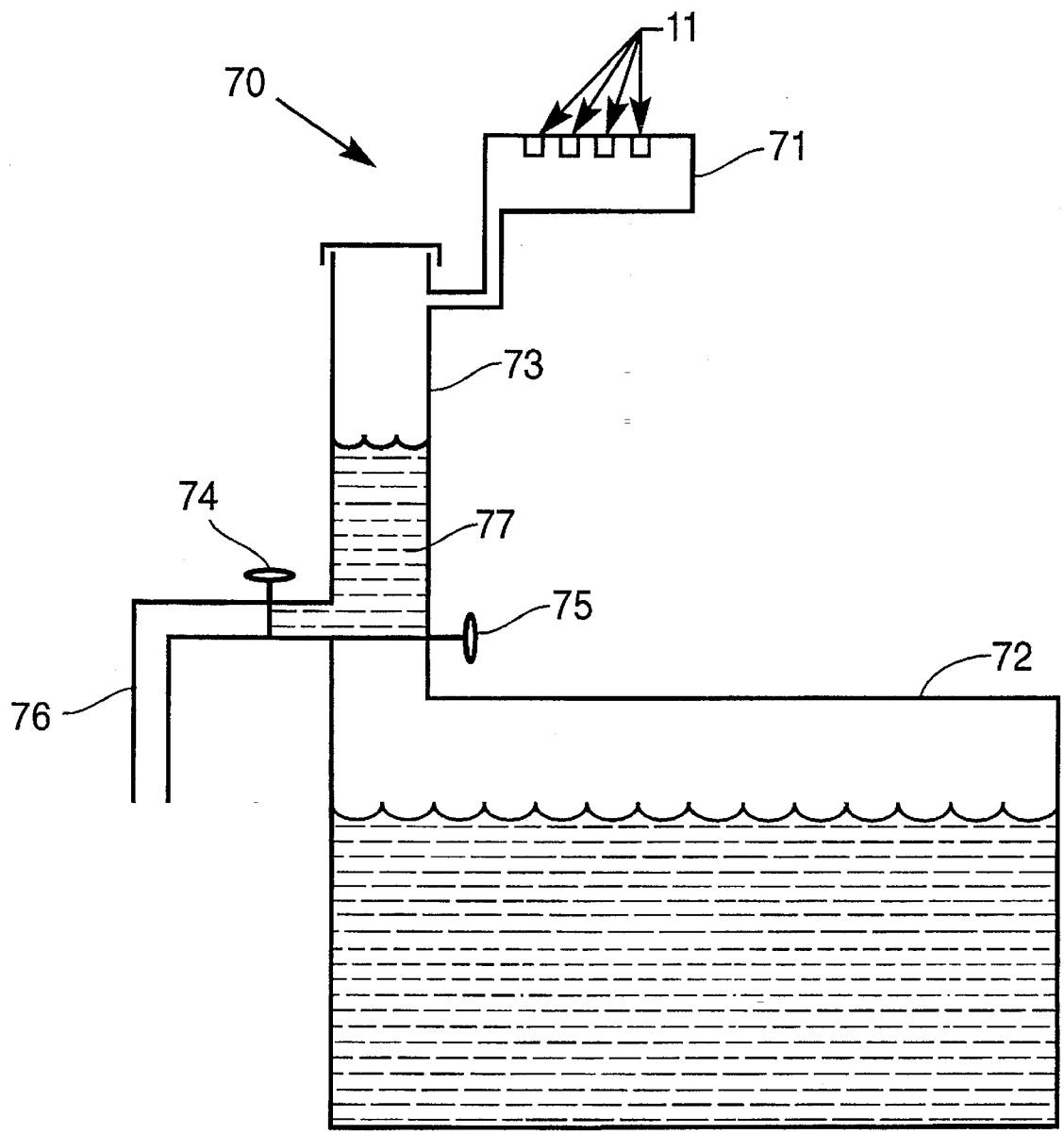
FIG. 13 shows one approach for incorporating the present invention directly into a vehicle.

The present invention can also be incorporated directly into a vehicle, preferably as an integral part of the fueling system. An embodiment of this device is shown in FIG. 13. In the system 70, a sensor array 11 is disposed in the chamber 71 such that the array 11 is exposed to fuel vapor but not to direct contact with the liquid fuel in the tank 72 or filler neck 73. Valves 74 and 75 are disposed to selectively isolate the filler neck 73 from the tank 72 and drain 76. A small sample of fuel to be tested 77 is introduced into the neck 73 after closing valves 74 and 75. Vapor from the fuel sample 77 accumulates in the chamber 71 allowing analysis of the fuel according to the method of the present invention. If the fuel is determined not to be acceptable, valve 74 is opened to discharge the sample through drain 76. If the fuel is determined to be acceptable, valve 75 is opened and fueling can safely commence.

Figure 14:
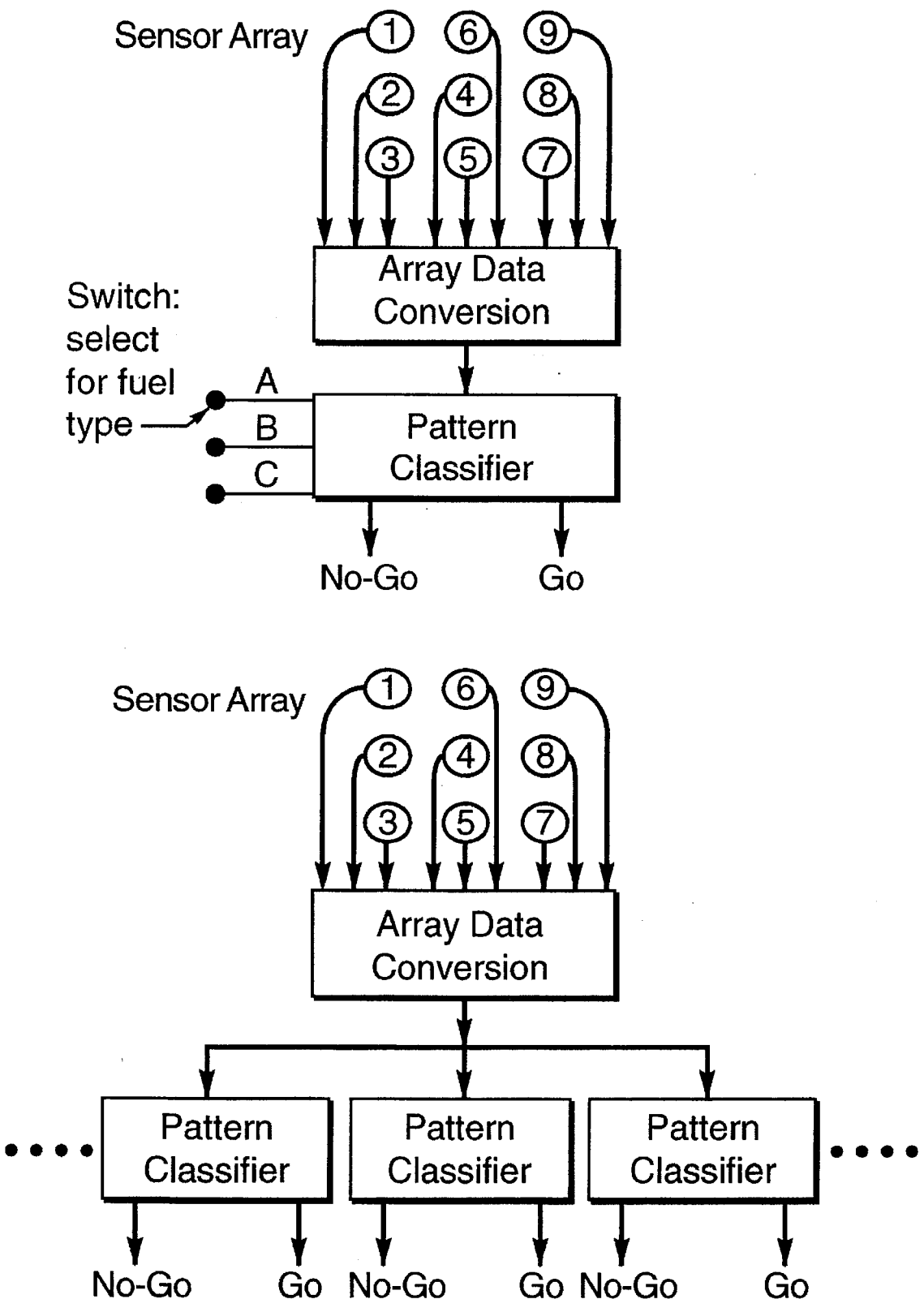
FIG. 14 is a block diagram of a system wherein the pattern classes are selectable by the user.

Another embodiment of the present invention incorporates features of both the general instrument, FIGS. 1 and 2, and the vehicle-specific instrument, FIGS. 11 and 12. In this embodiment, FIG. 14, the pattern classifier can be switched among various preprogrammed settings, each of which corresponds to a particular engine or vehicle or a specific type of fuel. The instrument then provides a go/no-go response for the selected classification "window".

EXAMPLE 6

Figure 7:
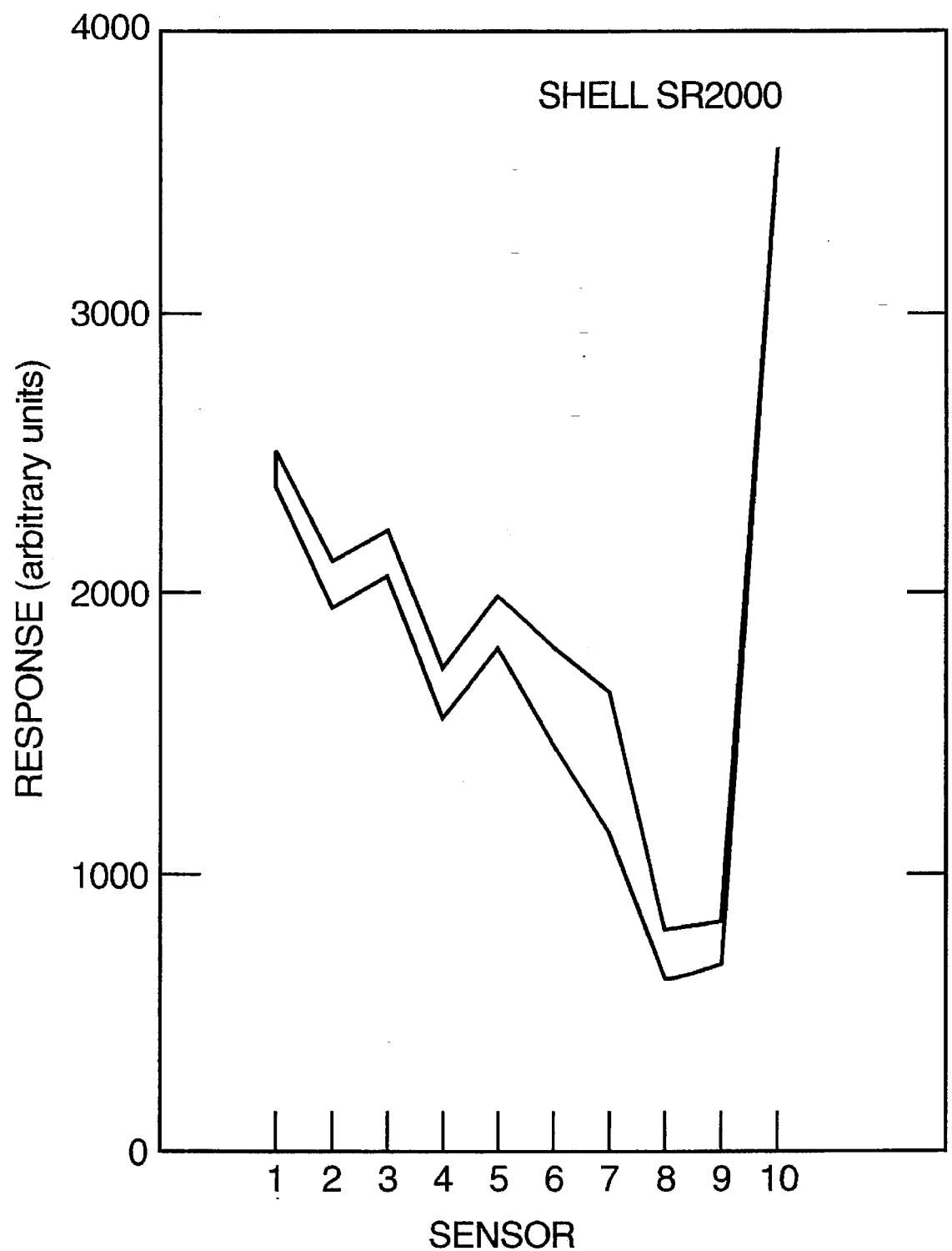
FIG. 7 is a graph illustrating the signature of an 89 ON motor fuel.
Figure 8:
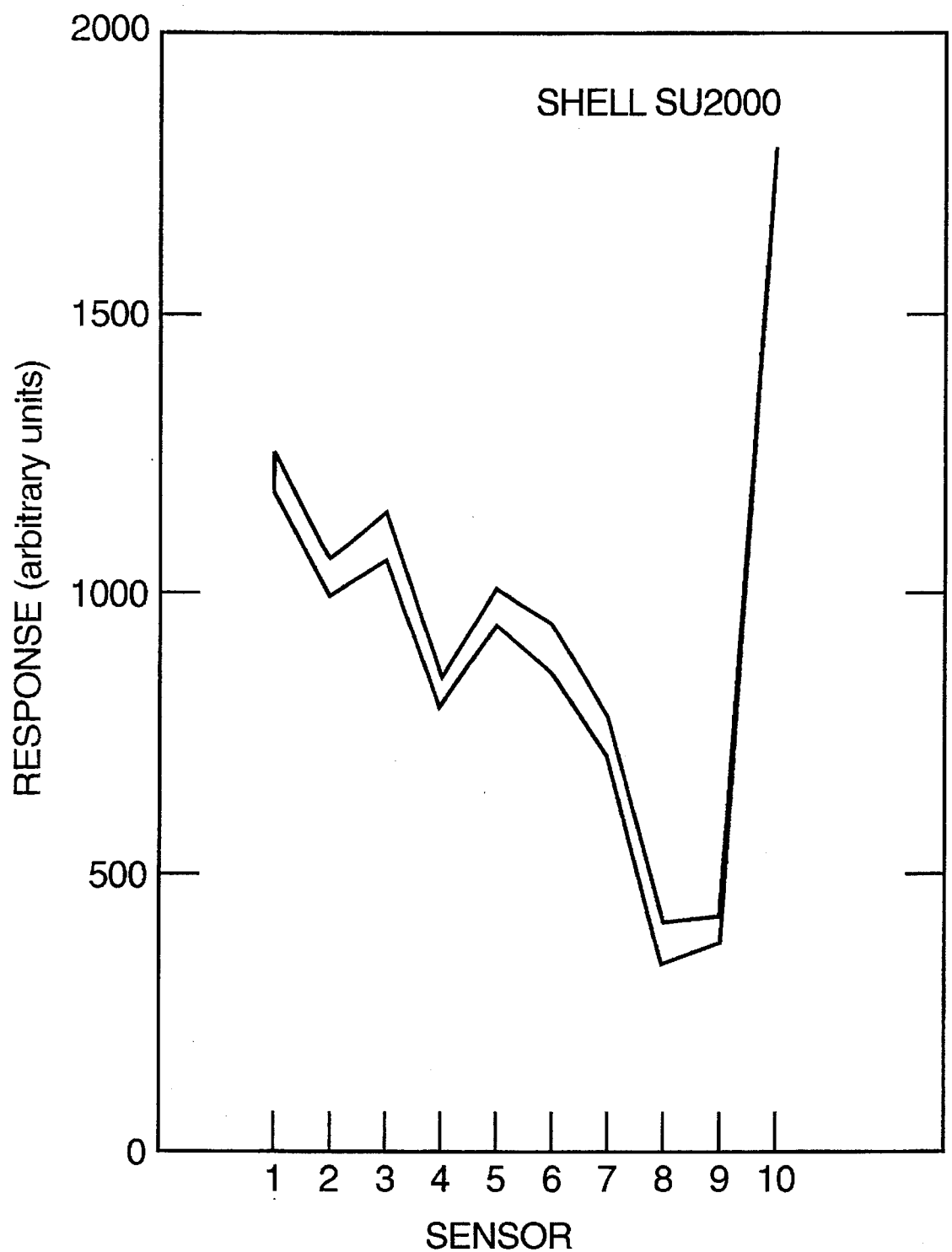
FIG. 8 is a graph illustrating the signature of a 92 ON motor fuel.
Figure 9:
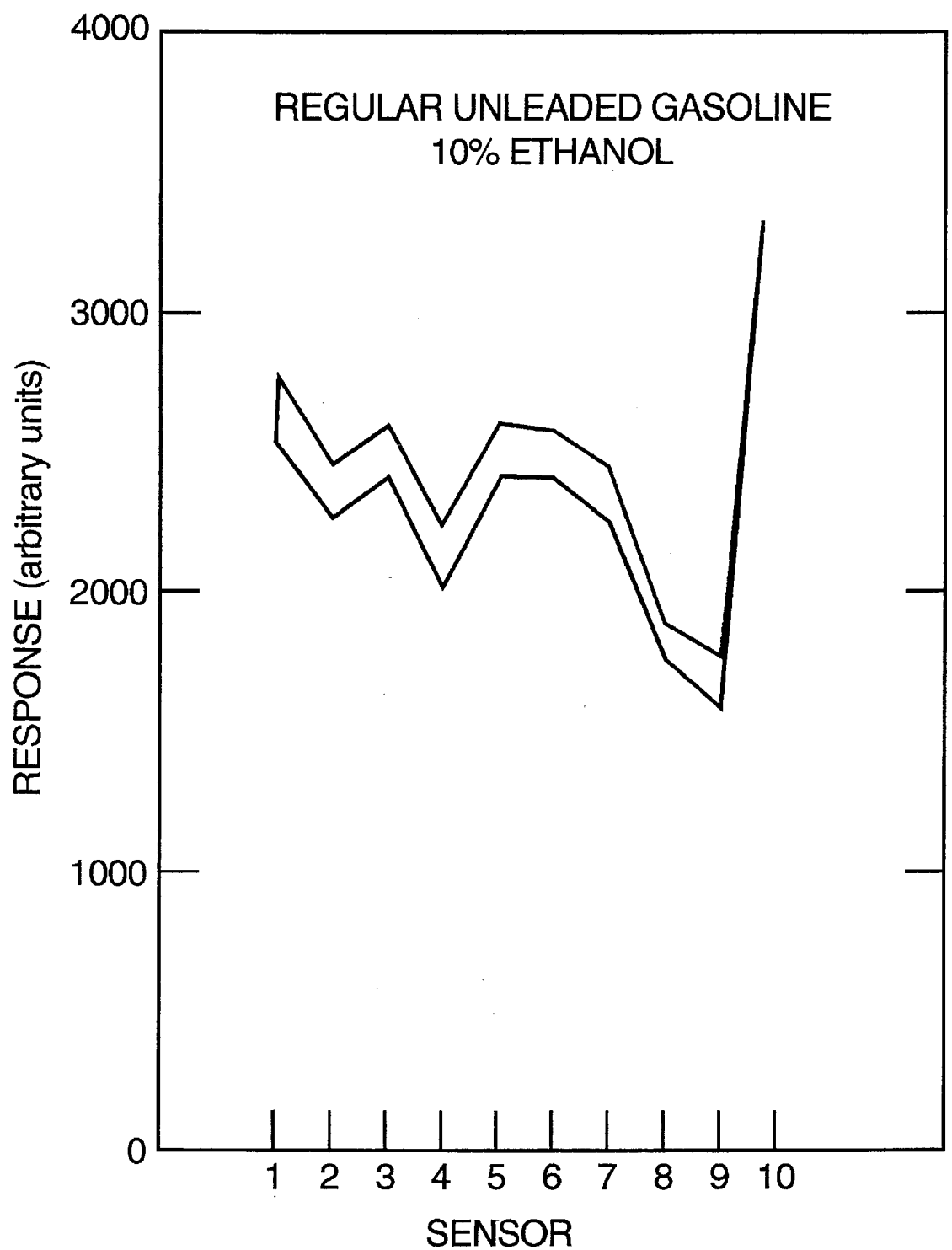
FIG. 9 is a graph illustrating the signature of a 93 ON motor fuel with 10% ethanol.

"Straight" gasolines, from a variety of sources and with a variety of octane values, have similar signatures as typified by FIGS. 6–8, which are quite different from those of gasoline-alcohol blends as typified by FIG. 9. It would therefore be straight forward to classify commercial motor fuels with respect to the presence or absence of alcohol and provide a go/no-go indication thereof.

EXAMPLE 7

Motor fuels with octane values from 87 to 92, with or without alcohol, have signatures that are quite different from that of 100 octane low lead aviation gasoline. All types of jet fuel also have signatures much different from that of gas. A specific pattern classifier set to recognize only 100 octane low-level fuel could therefore protect a piston-engine light aircraft from misfueling with either jet fuel or motor gasoline.

EXAMPLE 8

The signatures of Jet A (commercial) and JP-5 (military) are very similar, and different from other aviation fuels. These two fuels can be safely interchanged because of their similar composition and properties and can, at the same time, be distinguished from fuels that cannot safely be substituted for them. An analogous problem is identifying aviation fuels which not only have appropriate de-icers included therein, but also where the de-icer has properly remained in solution. The present invention also solves this problem.

929-X
B. S. Hoffheins et al

APPENDIX

Bit Pattern Conversion Program (35)

```c
/* transfer data into bit patterns */ include <io.h>
include <stdio.h>
#include <math.h>
#include <fcntl.h>
#include <sys\types.h>
include <sys\stat.h> define FIRST_CHN 0
define LAST_CHN 9 int    char_to_integer (numb,j)
char   numb[1000];

{
    int i, integer_value, result = 0,  mult=10000;

for ( i = j; i<5+j; ++i, mult=mult/10)
    {
      if(numb[i] >= '0' && numb[i] <= '9')

{
            integer_value = (numb[i] - '0')*mult;
            result = result + integer_value;

}
    } return (result);
}
```

929-X
B. S. Hoffheins et al

```
main()
{
  FILE *input;
  char inrec[120];
  int data[10][16], chn, matrix[10][10];

int recno=0;
  int fo, fi, lseek, i, j, k, l, num_array[2][10], gap[10];
  int arraysize;
  int scale ;
  static int sensornum[10]={0,0,0,0,0,0,0,0,0,0};
  unsigned int letter, bytes;
  char bb[1000], filename[15], chars[2][10];
  char bitpat[11][16][5], warray[16][11][5];
  static char high[] = { " 0.5," }, low[] = { "-0.5," };
  static char beg[] = { " /*" }, end[] = { "*/" };

printf ("Enter the data file name: ");
scanf ("%s",filename);
printf ("Filename is %s\n", filename);
printf ("\n");

printf ("\nEnter the array size: ");
  scanf ("%d",&arraysize);

if (arraysize == 10 )
    { for (i=0; i<10; ++i)
        sensornum[i]= 1;
    }
 else
   {
     for (i=0; i < arraysize; ++i)
     {
       printf ("\nEnter the sensor number %d:\n ",i);
       scanf ("%d", &j);
       sensornum[j]=1;
```

21

```
            }
          } for (i=0; i<10; ++i)
          {
/*        printf ("%d: %d\n",i, sensornum[i]);*/
          } input = fopen (filename, "r");
      recno = 0;

while (!feof(input))
      {
        fgets(inrec, 80, input);

if (strlen(inrec) < 72)
           continue;

{
        sscanf(inrec, "%d%d%d%d%d%d%d%d%d%d%d%d%d%d%d%d",
              &data[recno][0],&data[recno][1],&data[recno][2],&data[recno][3],
              &data[recno][4],&data[recno][5],&data[recno][6],&data[recno][7],
              &data[recno][8],&data[recno][9],&data[recno][10],&data[recno][11],
  &data[recno][12],&data[recno][13],&data[recno][14],&data[recno][15]);
        ++recno;
        }
      }
      fclose (input);

scale = 256;

for (j=0; j<recno; ++j)
  {
      for (i=0; i<16; ++i)
      {
```

```
/*      printf( "%d: %d ", data[j][i],data[j][i]/scale);*/
    }
  printf("\n");
}

/* assign num_array[][] for 5-10 minute data  (recno = 7,8) */ for (i=0; i<10; ++i)
           {
             num_array[1][i]=data[7][i];
             num_array[2][i]=data[8][i];
             printf("%d %d  ",num_array[1][i],num_array[2][i]);
             printf("%d %d %d \n",scale, num_array[1][i]/scale,
                     num_array[2][i]/scale);
           }

/* find the "hits" and calculate range */
  for (i=0;i<10;++i)
      {
        gap[i]=num_array[2][i]/scale-num_array[1][i]/scale;
/*      printf("gap %d is %d\n",i,gap[i]);*/
      }

/* open file for writing */ if (( fi = open("new.dat", O_CREAT| O_RDWR| O_APPEND| O_TEXT )) == -1)
     { perror ("open failed on output file");

exit (1);
     }

/* write header in file for "filename" */ if ( bytes = write( fi,"     \r\n\r\n"    , 7) == -1)
      perror ("");

if ( bytes = write( fi,beg,strlen(beg)) == -1)
      perror ("");
```

```
if ( bytes = write( fi,filename, strlen(filename)) == -1)
      perror ("");

if ( bytes = write( fi,end, strlen(end)) == -1)
      perror ("");

if ( bytes = write( fi,"   \r\n\r\n "      , 8) == -1)
      perror ("");

/* Convert to bit pattern */ for (k=0; k<16;++k)
{
      for (j=0,i=-1; j<11; ++j)
      {
         if (sensornum[j]==1 || j==10)
         {
            { ++i;
              if (j==10)
                     strcpy (warray[k][i], "  \r\n");
              else if (num_array[1][j]/scale == 15-k)
                     strcpy (warray[k][i], high);
              else if (num_array[2][j]/scale == 15-k)
                     strcpy (warray[k][i], high);
              else if (15-k < num_array[1][j]/scale && 15-k >
                     num_array[2][j]/scale)
                     strcpy (warray[k][i], high);
              else if (15-k > num_array[1][j]/scale && 15-k <
                     num_array[2][j]/scale)
                     strcpy (warray[k][i], high);
              else
                     strcpy (warray[k][i],low);
            }
            if ( bytes = write( fi,warray[k][i] , 5) == -1)

perror ("");
         }
      }
}
```

```
        } for (i=0;i<16;++i)
        {
                printf ("%s",warray[i]);
        }
close (fi);
}
```

929-X
B. S. Hoffheins et al

Data Acquisition Program (36)

```
1000 'Program to display and store sensor array data
1010 'First, set up parameters:
1020 '   1.  name data file
1030 '   2.  duration of test (type 1 test is 30 minutes)
1040 '   3.  time intervals for data acquisition (type 2 test only)
1050 PRINT "enter base file name:"
1060 INPUT FILE$
1070 NEWFILE$=LEFT$(FILE$,3)+"-"+LEFT$(TIME$,2)+MID$(TIME$,4,2)+".dat"
1080 OPEN "o",#2, NEWFILE$
1090 PRINT #2, FILE$+"    "+DATE$+"    "+TIME$+CHR$(13)+CHR$(10)
1100 '
1110 PRINT "Use the default time array? (Y/N)": INPUT ANSWER$
1120 IF ANSWER$ = "y" THEN GOTO 1240
1130 IF ANSWER$ = "Y" THEN GOTO 1240
1140 TYPE=2
1150 PRINT "Enter the time period of the test in minutes."
1160 INPUT TESTLENGTH: PRINT "test length =",TESTLENGTH
1170 TESTLENGTH=TESTLENGTH*60
1180 PRINT "Enter the interval period in seconds."
1190 INPUT INTERVAL: PRINT "interval =",INTERVAL
1200 NUMTESTS=INT(TESTLENGTH/INTERVAL)
1210 PRINT #2, "Test length=";TESTLENGTH;"seconds";CHR$(13)
1211 PRINT #2, "No. of tests=";NUMTESTS;CHR$(13)
1230 GOTO 1400
1240 NUMTESTS=12
1250 TYPE = 1
1251 PRINT #2, "Test length = 30 minutes.";CHR$(13)
1252 PRINT #2, "No. of tests = 12";CHR$(13)
1253 PRINT #2, "(Default test mode)";CHR$(13);CHR$(10)
1260 DIM TA(NUMTESTS+1)
1270 TA(0)=0
1280 TA(1)=.25
1290 TA(2)=.5
1300 TA(3)=.75
1310 TA(4)=1
1320 TA(5)=2
1330 TA(6)=3
1340 TA(7)=4
1350 TA(8)=5
1360 TA(9)=10
1370 TA(10)=15
1380 TA(11)=20
1390 TA(12)=30
1400 DIM SIGNATURE(NUMTESTS,16),TIMES(1000)
1410 DIM FILEARRAY(12,16)
1420 '------------ INITIAL SCREEN PRE-AMBLE ---------------------------
1430 SCREEN 0,0,0:WIDTH 80:CLS: KEY OFF
1440 '------ Loading DASH16.BIN at 192K (Hex 3000) outside BASIC workspace -----
```

```
1450 'This method is simpler than contracting workspace, but you have to be
1460 'sure you are loading into an unused part of memory.
1470 '
1480 ' Set current segment to load segment
1490 DEF SEG = &H3000     'for example only, try other segments
1500 ' Next, load DASH16.BIN at zero offset from this segment
1510 BLOAD "DASH16.BIN",0
1520 ' We are now free to use the subroutine. Your first CALL should be Mode 0
1530 ' to initialize the routine with DASH16's I/O location, interrupt etc.
1540 '
1550 DIM DIO%(4)    'dimension data I/O array for calls
1560 ' The I/O location is contained in the DASH16.ADR file which is generated
1570 ' by the INSTALL.BAS program. If you pick up the I/O location in all your
1580 ' programs in this manner, it will make it very easy for you to relocate
1590 ' the I/O address of DASH8 without changing all your programs.
1600 '
1610 OPEN "DASH16.ADR" FOR INPUT AS #1
1620 INPUT #1, DIO%(0)
1630 CLOSE #1
1640 '
1650 ' The alternative is for each program to assign the I/O address:-
1660 ' e.g. DIO%(0) = &H310
1670 '
1680  DIO%(1) = 2  'Set interrupt level that you want to use (2 thru 7)
1690  DIO%(2) = 3  'Set D.M.A. level that you want to use (1 or 3)
1700 '
1710 ' Now define the offset variable DASH16 for the CALL to be zero
1720 DASH16 = 0
1730 ' And set the error flag to zero:-
1740 FLAG% = 0
1750 ' And the mode number to zero:-
1760 MD% = 0
1770 ' Now run the initialize:-
1780 CALL DASH16 (MD%, DIO%(0), FLAG%)
1790 'The FLAG% variable can tell you if anything went wrong:-
1800 IF FLAG% = 0 THEN PRINT "O.K., DASH16.BIN INSTALLED AND INITIALIZED"
1810 IF FLAG% = 2 THEN PRINT "DASH16.BIN INSTALLED, BUT MODE NUMBER OUT OF RANGE
. NOT INITIALIZED"
1820 IF FLAG% = 3 THEN PRINT "DASH16.BIN INSTALLED, BUT BASE ADDRESS INVALID."
1830 IF FLAG% = 4 THEN PRINT "DASH16.BIN INSTALLED, BUT INTERRUPT LEVEL INVALID.
"
1840 IF FLAG% = 5 THEN PRINT "DASH16.BIN INSTALLED, BUT D.M.A. LEVEL INVALID."
1850 IF FLAG% = 22 THEN PRINT "DASH16.BIN INSTALLED, BUT DASH-16 HARWARE NOT PRE
SENT OR INCORRECT I/O ADDRESS"
1860 GOTO 2290
1870 '
1880 'An uncommented version of lines 2000 - 2340 suitable for merging into
1890 'your own programs starts on line 20000
1900 '
1910 '
1920 '
1930 '
```

```
1940 CLEAR, 49152!
1950 DEF SEG = 0
1960 SG = 256 * PEEK(&H511) + PEEK(&H510)
1970 SG = SG + 49152!/16
1980 DEF SEG = SG
1990 BLOAD "DASH16.BIN", 0
2000 DIM DIO%(4)
2010 OPEN "DASH16.ADR" FOR INPUT AS #1    'get base I/O address
2020 INPUT #1, DIO%(0)
2030 DIO%(1) = 2
2040 DIO%(1) = 2                          'interrupt level
2050 DIO%(2) = 3                          'D.M.A. level
2060 DASH16 = 0                           'call offset - always zero
2070 FLAG% = 0                            'error variable
2080 MD% = 0                              'mode 0 - initialize
2090 CALL DASH16 (MD%, DIO%(0), FLAG%)
2100 IF FLAG%<>0 THEN PRINT "INSTALLATION ERROR":STOP 'Halt on error
2110 'Continue your program from here
2120 '
2130 '
2140 '
2150 DEF SEG = &H3000   'Change this load address to suit your memory
2160 BLOAD "DASH16.BIN",0
2170 DIM DIO%(4)
2180 OPEN "DASH16.ADR" FOR INPUT AS #1    'get I/O base address
2190 INPUT #1, DIO%(0)
2200 CLOSE #1
2210 DIO%(1) = 2                          'interrupt level
2220 DIO%(2) = 3                          'D.M.A. level
2230 DASH16 = 0                           'call offset - always zero
2240 FLAG% = 0                            'error variable
2250 MD% = 0                              'mode 0 - initialize
2260 CALL DASH16 (MD%, DIO%(0), FLAG%)
2270 IF FLAG%<>0 THEN PRINT "INSTALLATION ERROR":STOP 'Halt on error
2280 'Continue your program from here
2290 'a/d acquisition
2300 MD% = 3
2310 CLS:COLOR ,1
2320 PRINT "              SENSOR ARRAY OUTPUT" ,DATE$, TIME$
2330 M=0:TIMES(0)=0
2340 T1=TIMER
2350 REM loop here
2360 M=M+1 : IF M>NUMTESTS THEN 2670
2370 IF TYPE = 1 THEN  2640
2380 TIMES(M)=TIMES(M-1)+INTERVAL
2390 IF (TIMER-T1)>=INTERVAL THEN T1=TIMER:GOSUB 2410
2400 GOTO 2390
2410 'a/d acquisition subroutine
2420 FOR I% = 1 TO 16
2430 CALL DASH16 (MD%, DIO%(0), FLAG%)
2440 SIGNATURE(M,I%) = DIO%(0)
2450 NEXT I%
2460 CLS
```

```
2470 PRINT "            SENSOR ARRAY OUTPUT" ,DATE$, TIME$
2490 PRINT "SNSR        READINGS (bits for indicated time in minutes)"
2491 PRINT
2500 PRINT "     ";
2510 S =2^INT(M/13)
2520 FOR J=1 TO M STEP S
2530 PRINT USING " ##.##";TIMES(J)/60;
2540 NEXT J
2550 PRINT:PRINT
2551 PRINT#2,CHR$(13)
2560 FOR I%=1 TO 16
2570 PRINT USING "##: ";I%;
2571 PRINT #2, USING"#### "; SIGNATURE(M,I%);
2580 FOR N=1 TO M STEP S
2590 PRINT USING "##### ";SIGNATURE(N,I%);
2600 NEXT N
2610 PRINT
2620 NEXT I%
2630 RETURN 2350
2640 INTERVAL=(TA(M)-TA(M-1))*60
2650 TIMES(M)=TA(M)*60
2660 GOTO 2390
2670 CLOSE#2
2671 STOP
```

We claim:

1. A system for classifying mixtures of hydrocarbon fuels according to octane or cetane number comprising:

an array of gas sensors having different response characteristics to the vapors of different known and unknown fuels such that the set of responses for each of said fuels forms a distinctive signature pattern with respect to octane or cetane number of said fuels, said array comprising at least four sensors;

a data acquisition system coupled to said sensor array for deriving said distinctive signature patterns of said known fuels, said data acquisition system comprising at least an analog-to-digital convertor; and a data analysis system comprising at least a neural network coupled to said data acquisition system for comparing the pattern of a sampled fuel mixture to the signature pattern of said known fuels whereby said sampled signature pattern of octane or cetane number is classified with respect to said known patterns of octane or cetane numbers by said neural network.

2. The system of claim 1 wherein said data acquisition system and said data analysis system are incorporated in a digital computer, and wherein said analog-to-digital convertor is a multiple channel analog-to-digital circuit within said digital computer, said analog-to-digital circuit being connected to said gas sensors to receive said set of responses.

3. The system of claim 2 wherein said data acquisition system further includes a bit pattern conversion program running in said digital computer.

4. The system of claim 2 wherein said neural network is a software neural network program operating within said digital computer.

5. The system of claim 2 wherein said data acquisition system further includes a computer program controlling the acquisition of gas sensor data by said analog-to-digital convertor.

6. The system of claim 1 wherein at least one of said gas sensors is an independently heated gas sensor.

7. The system of claim 1, wherein the differences in said response characteristics of at least some of said gas sensors result from differences in their preparation.

8. The system of claim 1, wherein the differences in said response characteristics of at least some of said gas sensors result from differences in their operating temperature.

9. The system of claim 1, wherein at least one of said gas sensors is a semiconductor sensor.

10. The system of claim 1, wherein at least one of said gas sensors is a solid state sensor.

11. The system of claim 1, wherein at least one of said gas sensors is a homogeneous semiconductor gas sensor.

12. The system of claim 1, wherein the differences in said response characteristics of at least some of said gas sensors result from differences in their composition.

13. The system of claim 1, wherein said neural network is a software neural network program stored on a programmable memory chip.

14. The system of claim 1, wherein said data analysis system is an application-specific integrated circuit comprising at least a neural network processor.

15. The system of claim 1 wherein said array of gas sensors is fabricated onto a single substrate.

16. A system according to claim 1, wherein said array of gas sensors is fabricated into a single sensor head.

17. The system of claim 16 further including a plurality of said sensor heads, each in separate locations dispersed about an environment, and means responsive to signals derived from all of said sensors of said heads to determine the identities fuel mixtures present at each of said locations.

18. The system of claim 1 wherein said known fuel mixtures are taken from the group of liquid fuels comprising gasoline, diesel fuel, aviation fuel, and gasohol.

19. The system of claim 18 wherein said array of gas sensors additionally have different response characteristics to the vapors of different known and unknown fuels such that the set of responses for each of said fuels additionally forms a distinctive signature pattern with respect to oxygenate or deicer content and wherein said neural network can additionally classify said sampled signature pattern with respect to said know patterns of oxygenate or deicer content.

20. The system of claim 1 wherein said gas sensor array comprises metal oxide gas sensors.

21. The system of claim 1 wherein said data acquisition system further includes a bit pattern conversion means for converting said signature patterns into bit patterns.

22. The system of claim 1 wherein said neural network is a Hamming network.

23. The system of claim 1 wherein said neural network is a Boltzmann network.

24. The system of claim 1 wherein said array of gas sensors includes at least ten sensors and wherein at least one of said sensors is dissimilar from the other sensors.

25. A method identifying mixtures of hydrocarbon fuels according to octane or cetane number comprising the steps of:

selecting an array of gas sensors, each of said sensors having different response characteristics to the vapors of different known fuels such that the set of sensor responses to each of said known fuels forms a distinctive signature pattern with respect to the octane or cetane number of said fuels, said array of sensors comprising at least four sensors;

deriving said signature patterns of said known fuels by analog-to-digital conversion means; and analyzing the signature pattern of a sampled fuels with respect to the signature patterns of said known fuels by neural network means whereby said sampled signature pattern of octane or cetane numbers is classified with respect to said known signature patterns of octane or cetane numbers.

26. The method of claim 25 including the further step of controlling said analog-to-digital conversion means by a data acquisition computer program.

27. The method of claim 25 wherein said neural network means is a software neural network program operating within a digital computer.

28. The method of claim 25 wherein said known fuel mixtures are taken from the group of liquid fuels comprising gasoline, diesel fuel, aviation fuel, and gasohol.

29. The method of claim 25 including the further step of converting said signature patterns to bit patterns by a bit pattern conversion means.

* * * * *